United States Patent
Laugeman

(10) Patent No.: US 9,212,339 B2
(45) Date of Patent: Dec. 15, 2015

(54) CLEANSING COMPOSITION

(75) Inventor: Frits Jan Rudolf Laugeman, Tilburg (NL)

(73) Assignee: Laugeman Laboratories B.V., Rotterdam (NL)

( * ) Notice: Subject to any disclaimer, the term of this patent is extended or adjusted under 35 U.S.C. 154(b) by 475 days.

(21) Appl. No.: 12/158,918

(22) PCT Filed: Dec. 29, 2006

(86) PCT No.: PCT/EP2006/012656
§ 371 (c)(1),
(2), (4) Date: Oct. 16, 2008

(87) PCT Pub. No.: WO2007/077039
PCT Pub. Date: Jul. 12, 2007

(65) Prior Publication Data
US 2010/0068158 A1    Mar. 18, 2010

(30) Foreign Application Priority Data
Dec. 30, 2005 (EP) ..................... 05078067

(51) Int. Cl.
*C11D 3/48* (2006.01)
*A61K 8/19* (2006.01)
*A61K 31/19* (2006.01)
*A61K 31/60* (2006.01)
*A61Q 11/00* (2006.01)
*C11D 7/26* (2006.01)

(52) U.S. Cl.
CPC ... *C11D 3/48* (2013.01); *A61K 8/19* (2013.01); *A61K 31/19* (2013.01); *A61K 31/60* (2013.01); *A61Q 11/00* (2013.01); *C11D 7/265* (2013.01)

(58) Field of Classification Search
CPC ......... A61K 31/19; A61K 31/60; A61K 8/19; A61Q 11/00; C11D 3/48; C11D 7/265
See application file for complete search history.

(56) References Cited

U.S. PATENT DOCUMENTS

| | | | |
|---|---|---|---|
| 6,106,851 A * | 8/2000 | Beerse et al. | 424/401 |
| 6,239,088 B1 * | 5/2001 | George et al. | 510/131 |
| 2003/0100101 A1 | 5/2003 | Huth et al. | |
| 2004/0067204 A1 | 4/2004 | Wolf | |
| 2004/0076591 A1 | 4/2004 | Anthony Nelson et al. | |
| 2004/0077609 A1 | 4/2004 | Rubin et al. | |
| 2004/0265396 A1 * | 12/2004 | Peshoff | 424/643 |
| 2005/0058719 A1 | 3/2005 | Ramirez et al. | |
| 2005/0142215 A1 * | 6/2005 | Kling | 424/661 |
| 2006/0057078 A1 * | 3/2006 | Rau | 424/49 |

FOREIGN PATENT DOCUMENTS

| | | |
|---|---|---|
| EP | 1314419 A2 | 5/2003 |
| WO | WO0128339 A2 | 4/2001 |

* cited by examiner

*Primary Examiner* — Kara R McMillian
(74) *Attorney, Agent, or Firm* — Bret E. Field; Makoto Tsunozaki; Bozicevic, Field & Francis LLP

(57) ABSTRACT

The present invention relates to a cleansing composition comprising an anti-microbial agent and a sulphur binding and/or oxidizing agent, and wherein the pH of the composition is 7 or lower, to a method for preparing the cleansing composition and its use.

14 Claims, No Drawings

CLEANSING COMPOSITION

The present invention relates to a cleansing composition comprising an anti-microbial agent, a first sulphur binding and/or oxidising agent, and optionally a second sulphur binding and/or oxidising agent, and wherein the pH of the composition is 7 or lower, to a method for preparing the cleansing composition and its use.

At the present various cleaning compositions are used in dental care. They are for example used for cleaning dental braces or prostheses, such as artificial teeth. Another use of these cleansing compositions is their use as an oral rinse composition for the treatment of halitose, i.e. breath malodour or for the treatment of periodontitis.

In the mouth and on dental braces and prosthesis food residues and cellular debris accumulate. Due to the breakdown of these residues by oral micro-organisms, in particular due to the breakdown of sulphur containing amino-acids, volatile sulphur compounds are formed. These volatile sulphur compounds cause a bad breath or smell of the braces or prostheses. Moreover, the accumulation of cellular debris and food residues provide an excellent environment for growth of oral micro-organisms such as for example *P. gingivalis, Peptostreptococcus* spp and *P. intermedia*. These micro-organisms do not only cause malodour but also cause periodontitis and pathological periodontal pockets causing considerable discomfort for patients.

In the art several solutions have been proposed to overcome periodontitis, bad breath or smell of the braces or prostheses. One of the generally applied methods is to use rinse compositions for rinsing the mouth or the braces. These rinse compositions oxidise the volatile sulphur compounds such that no bad smell develops. Other rinse compositions have an anti-microbial effect on the micro-organisms present in the mouth, which organisms are responsible for causing periodontitis or for break down of the amino acids. This way periodontitis, malodour of the mouth or the braces or prostheses is partially avoided.

Compositions presently used for overcoming periodontitis, a bad breath or smell of braces or prostheses comprise for example chlorohexidine. The effect of chlorohexidine is obtained through its anti-bacterial effect, i.e. its anti-bacterial effect on mainly gram negative bacteria. However, chlorohexidine has several disadvantages. One of the most important disadvantages is that if a patient rinses his mouth with chlorohexidine compositions regularly, his teeth and tongue obtain a brownish colour. This is off course a major disadvantage. Another disadvantage of chlorohexidine is that it has no significant anti-bacterial effect on gram positive bacteria at relatively low concentrations. This means that gram positive bacteria will not be effected by the rinse composition and may thus still cause periodontitis or produce the volatile sulphur compounds that cause the malodour.

Other compositions presently used for treating halitose or for the cleaning of braces or prostheses comprise chlorite. The effectiveness of these compositions is obtained when chlorite contacts acids produced by oral bacteria which trigger the formation of chlorine dioxide whereby the odour causing volatile sulphur compounds are destroyed, i.e. oxidized. These compositions are thus only used for breakdown, i.e. oxidation of odour causing compounds, instead of reducing the amount of oral micro-organisms.

For example U.S. Pat. No. 5,772,986 describes a kit comprising a first acidic composition for creating an acidic environment in the mouth and a second composition comprising chlorite. Due to the pre-acidification of the mouth with the first composition the efficacy of the second composition comprising chlorite increases. However the disadvantage of this composition is that a kit has to be used which comprises two compositions, one for acidification and one for breakdown of the sulfur chlorite compounds. Moreover, by using chlorite, only breakdown of the odour causing compounds is obtained without a considerable reduction of oral micro-organisms.

An object of the present invention is to overcome the problems associated with the cleansing compositions presently used.

A first aspect of the present invention relates to cleansing composition comprising an anti-microbial agent, a first sulphur binding and/or oxidising agent, and optionally a second or further sulphur binding and/or oxidising agent, and wherein the pH of the composition is 7 or lower.

An advantage of the present invention is that one composition can be used for both anti-microbial and chemical control of malodour. A further advantage is that the present composition is active against a broad variety of micro organisms such as gram negative and gram positive bacteria, yeast and fungi. Another advantage of the present invention is that only one composition has to be used in stead of a kit comprising a first and a second composition such as described in U.S. Pat. No. 5,772,986. Further, by using the composition according to the invention slime and food residues present in the mouth or on dental braces or prostheses can be removed causing inactivation of the micro-organisms present therein. Moreover, calcium deposits present on the teeth or on the dental braces or prostheses can be removed by using the composition according to the invention.

Another important advantage of the present invention is that the dental braces or prostheses that are treated with the composition according to the invention are substantially free from oral micro-organisms. Generally dental braces and prostheses are made of porous materials providing a suitable environment for micro-organisms. However due to the treatment with the composition according to the invention micro-organisms and food residues in the porous matrix of the dental braces and/or prostheses are removed. Particularly when patients have previously been treated for periodontitis it is advantageous if the braces and/or prostheses are substantially free of micro-organisms, such that re-contamination of the cleaned places is avoided. It is further noted that the present cleansing composition is preferably an aqueous composition. However, the composition may also be formulated as a dispersion, gel or paste (for example as toothpaste). However, a gel is preferred if the composition is used for cleaning of pathological periodontal pockets.

In an embodiment of the present invention the pH is in the range of 1 to 5, preferably 2-4. This pH range is advantageous for reasons that it creates an environment wherein micro-organisms may effectively be killed. Furthermore, a relatively low pH has a calcium binding effect. This effect is especially advantageous in the present invention for reasons that calcium accumulation may have taken place on the teeth or on the brace or prostheses resulting in a poor appearance thereof. Another advantage of the above mentioned pH range is that the slime layer formed by food residues and cellular debris present in the oral pharynx is at least partly destroyed. This destruction of the slime layer makes it possible that anaerobe bacteria, that cause periodontitis or a malodour, present under or in the slime layer can effectively be inactivated by the anti-microbial agent present in the composition. Moreover, due to the relatively low pH, proteins present in the mouth or on the dental braces or prostheses denaturate such that they can easily be removed.

The amount of the first sulphur binding and/or oxidising agent and/or second sulphur binding agent is between 0.005 and 1 wt %, preferably between 0.04 and 1 wt %, more preferably between 0.04 wt % and 0.3 wt %, most preferably between 0.1 and 0.3 wt %. Within these ranges the sulphur compounds formed by the bacteria are substantially removed, causing the malodour to disappear.

Particular preferred as the first sulphur binding/oxidising agent is ammonium. Ammonium is preferred because it is very reactive with sulphur compounds, thus taking away the malodour. Furthermore, ammonium also helps to dissolve fat-residues present in the mouth. This means that sulphur compounds contained in these fat residues (such as food debris) can be taken away. Furthermore, since the fat residues dissolve, the efficacy of the anti-microbial agent used in the present composition is increased. After all, the anaerobe bacteria contained in the fat residues are brought into contact with the anti-microbial agents more easily. The use of ammonium thus increases the efficacy of the cleansing composition.

It is even more preferred if the amount of ammonium in the composition is between 0.04 and 0.5 wt %, preferably between 0.1 and 0.5 wt %. Within this range the efficacy increases even more.

It is further preferred if the second sulphur binding/oxidising agent comprises calcium, sodium, sodium benzoate, a benzene-derivate, an aromatic hydrocarbon, acetyl salicylic acid or mixtures thereof. It may however also be possible that one or more of these sulphur binding/oxidising agents form the first sulphur binding/oxidising agent. By using one or more of these sulphur binding/oxidising agents reduction of the sulphur compounds present in the mouth, pharynx or on prostheses improves even further.

In a preferred embodiment the anti-microbial agent is an organic acid. The anti-microbial agent is more preferably a hydroxy acid, citric acid, acetic acid, acetyl salicylic acid, butyric acid, lactic acid, tartaric acid, and/or $NaHCO_2$. By using one of these anti-microbial agents the micro-organisms producing the sulphur compounds, i.e. causing the malodour, are substantially inactivated. This means that no substantial formation of a malodour will occur.

The amount of organic acid or acids in the composition preferably ranges from 1.0 to 50 wt %, preferably from 30 to 45 wt % or from 1 to 10 wt %. Within these ranges a particular good efficacy of the composition is obtained.

It is even more preferred if the amount of acetic acid in the composition ranges from 0.05 to 10 wt %, preferably from 1 to 10 wt %, more preferably from 1 to 6 wt %. Besides its efficacy as an anti-microbial agent it also dissolves fat. This means that fat residues from for example food residues are (partly) dissolved and that the sulphur binding/oxiding agents can easily bind or react with these compounds. Also the inactivation of micro-organisms present in the mouth, pharynx or on prostheses or instruments is improved.

Further, preferably tartaric acid is used as an organic acid. Tartaric acid provides an improved efficacy. Preferably the amount of tartaric acid ranges between 0.5 and 10 wt %, preferably between 0.5 and 3 wt %.

In a preferred embodiment according to the present invention the amount of the first sulphur binding/oxidising agent is between 0.1 and 0.8 preferably between 0.1 and 0.3 wt % of the composition, the amount of anti-microbial agent is between 30 to 45 wt % of the composition and the pH is between 2 and 4. Such an embodiment is particular suitable for use as a cleansing composition for cleaning prostheses, such as dental prostheses and braces, dental instruments such as surgical instruments and stainless steel dental and surgical instruments. Preferably, the first sulphur binding/oxidising agent is ammonium and the anti-microbial agent tartaric acid and/or acetic acid.

In another preferred embodiment the amount of the first sulphur binding/oxidising agent is between 0.03 and 0.15 wt % of the composition, the amount of anti-microbial agent is between 1 and 8 wt % of the composition and the pH is between 2 and 4. This embodiment is particularly suitable for use in the prophylaxes or treatment of disorders of the naso and/or oro pharynx, such as halitosis, periodontitis, gingivitis and/or the treatment of human skin or vaginosis. Preferably, the first sulphur binding/oxidising agent is ammonium and the anti-microbial agent tartaric acid and/or acetic acid.

The anti-microbial agent and the sulphur binding agent are preferably the same. This is advantageous for reasons that only one agent has to be used resulting in lower production and raw material costs. A preferred agent having both anti-microbial and sulphur binding properties is acetyl salicylic acid.

In a preferred embodiment of the present invention the amount of salicylic acid and/or $NaHCO_3$ 0.1 and 2.5 wt %. Salicylic acid is preferred for reasons that it has both anti-microbial properties and sulphur binding (oxidising) properties. Moreover, it has a anaesthetic effect. $NaHCO_3$ is preferred for reasons that it also improves the shelf-life of the composition.

In a specially preferred embodiment of the present invention the composition comprises a fluoride source. The addition of a fluoride source makes the cleansing composition particularly suitable for treatments in the mouth, particularly for use in the treatment of halitose, pathological peridontal pockets and/or periodontitis in the mouth. By using the fluoride source a possible demineralization of the teeth by the acidic composition is substantially avoided, whilst obtaining a reduction of oral micro-organisms and a break down of volatile sulphur compounds present in the mouth.

The fluoride source is preferably $NH_2F$, sodium fluoride, calcium fluoride, potassium fluoride, lithium fluoride, aluminium fluoride, zinc fluoride, zirconium fluoride, sodium monofluorophosphate, acidulated phosphate, fluoride, stannous chloro fluoride, magnesium fluoride, potassium trifluorostannous, titanium fluoride, iron fluoride, stannous hexafluorozirconate.

The composition preferably comprises between 0.05 and 0.5 wt % $NH_2F$ and/or NaF, preferably between 0.1 and 0.2 wt %, more preferably about 0.15 wt %.

Preferably the composition comprises enzymes such as lysozyme and/or lactoperoxidase. An advantage of the use of these enzymes is that an increased and faster anti-microbial effect is obtained when using the composition.

In order to make the composition more attractive colourings, flavourings and/or stabilisers may be added to the composition.

A second aspect of the present invention relates to a method for preparing the above mentioned composition, comprising the steps of: preparing a mixture of an anti-microbial agent, a first sulphur binding and/or oxidising agent, and optionally a second sulphur binding and/or oxidising agent, and adjusting the pH of the mixture to 7 or lower.

A third aspect of the present invention relates to a cleansing composition obtainable by the above mentioned method.

A fourth aspect of the present invention relates to the above mentioned composition for use as a medicament.

A fifth aspect of the present invention relates to the use of the above mentioned composition for the manufacture of a medicament for the treatment or prophylaxis of disorders of the naso and/or oro pharynx, such as halitose, periodontitis, gingivitis, cleansing of root (endodontic) canals and/or the treatment of human skin or vaginosis.

A sixth aspect of the present invention relates to the use of the above mentioned cleansing composition for cleansing prosthesis, such as dental prosthesis and braces, dental instruments, such as surgical instruments and stainless steel dental and surgical instruments.

Reference will now be made to the following examples intended to illustrate preferred embodiments of the invention but which are not to be construed as limiting the scope of this invention.

EXAMPLES

Example 1

Denture Cleansing Composition

An aqueous cleansing composition was prepared comprising 500 ml acetic acid (25%/l) as a calcium binding agent, 200 ml ammonia (10%/l $NH_3$) which in reaction becomes $NH_4^+$ which is a sulphur binding agent, 100 ml acethyl salicyclic acid (5%/l), and about 200 ml citric acid (5-10%/l) to lower the pH to 2. The composition further comprised a menthol flavouring for giving the composition a pleasant odour. Three used braces and two prostheses were immersed in the composition during about fifteen minutes. After the treatment no calculus, no debris and no malodour remained.

Example 2

Denture Cleansing Composition

An aqueous cleansing composition was prepared by preparing a mixture comprising about 0.15 wt % salicyclic acid, comprising about 2.5 wt % tartaric acid, about 6 wt % acetic acid, about 35 wt % citric acid and about 55 wt % water. The mixture also contained about 0.2 wt % ammonium obtained through the addition of ammonia to the aqueous mixture. For improving the taste and the smell of the mixture peppermint oil and sodium cyclamate was used. The composition obtained was particularly suitable for the cleansing of prosthesis such as sets of dentures.

The efficacy of the composition was tested by 158 persons all wearing dentures, such as partial dentures, frame prostheses and orthodontic braces. All respondents were asked to use the cleansing composition for cleaning their dentures and to note the time it took before the denture was substantially clean, i.e. until all food residues were substantially removed and the dentures did no longer have a malodour. As is clear from table 1, all respondents indicated that within 25 minutes their dentures were substantially clean and more than 50% of the respondents even indicated that their dentures were already clean after 15 minutes.

TABLE 1

| Time before denture is perceived as clean (min.) | Number of respondents |
| --- | --- |
| 10 | 15 |
| 15 | 73 |
| 20 | 43 |
| 25 | 27 |

As is clear from table 1 the cleansing composition according to the present invention had a relatively high efficacy.

Example 3

Instrument Cleansing Composition

In the same way as in example 2 the following composition was prepared for cleaning stainless steel dental instruments. The composition prepared comprises: about 0.5 wt % ammonium, about 0.15 wt % salicyclic acid, about 7.5 wt % tartaric acid, about 8.0 wt % acetic acid, about 27.5 wt % citric acid (monohydrate), about 1.5 wt % sodium cyclamate and about 55 wt % water. This composition was tested on 10 dental instruments (5 gingivectomy-knives; 5 dental-mirrors). All instruments were substantially clean within 15 minutes.

Example 4

Oral Cleansing Composition

An aqueous cleansing composition was prepared comprising about 25 mg per liter $NH_2F$ as a fluoride source, 100 ml ammonia (8%/l), 100 ml acethylsalicyl acid (5%/l), 400 ml acetic acid (20%/l), $NaHCO_3$ (4%/l) with Na as a second sulphur binding agent and $CO_3$ for oxidation, and about 500 ml citric acid (10-20%/l) to lower the pH to 3. Further, a menthol flavouring to give the composition a pleasant taste and sorbitol to sweeten the composition was added. Six patients suffering from halitosis rinsed their mouth twice a day during two minutes. After two weeks none of the patients suffered from halitosis.

Example 5

Oral Cleansing Composition

An aqueous cleansing composition was prepared comprising about 0.15 wt % salicyclic acid, about 0.15 wt % NaF, about 0.5 wt % $NHCO_3$, about 1.0 wt % lactic acid, about 1.0 wt % tartaric acid, about 1.2 wt % acetic acid, about 1.5 wt % citric acid, about 28 wt % sorbitol, about 0.1 wt % ammonium. This composition was tested among six patients suffering from halitosis and they we asked to rinse their mouth twice a day during two minutes. After two weeks none of the patients suffered from halitosis.

Example 6

Periodontitis Composition (Gel)

An aqueous cleansing composition was prepared comprising about 25 mg per liter $NH_2F$ as a fluoride source, 200 ml ammonia (12%/l), 100 ml acethylsalicyl acid (5%/l), 400 ml acetic acid (20%/l), 100 ml $NaHCO_3$ (4%/l), and 200 ml citric acid (10-20%/l) to lower the pH to pH 3. Also human enzymes were added to the composition, such as lysozyme and/or lactoperoxidase, or similar. Further, a menthol flavouring was added for improving the taste and sorbitol was added as a sweetener. Six patients rinsed their mouth twice a day during two minutes for three weeks. During this period they were treated for periodontitis with scaling and root planning of the pathological periodontal pockets and these pockets were irrigated with the same composition. This composition in a gel form was applied into the pathological pockets with a syringe for even greater effectiveness. After the treatment none of the patients suffered from periodontitis after six months.

Example 7

Periodontitis Composition (Solution)

An aqueous cleansing composition was prepared comprising about 0.1 wt % ammonium, about 0.15 wt % salicyclic acid, about 0.15 wt % NaF, about 0.75 wt % NaHCO$_3$, about 1.35 wt % lactic acid, about 1.5 wt % tartaric acid, about 1.2 wt % acetic acid, about 2.5 wt % citric acid, about 28 wt % sorbitol and about 64 wt % water. Six patients rinsed their mouth twice a day during two minutes for three weeks. During this period they were treated for periodontitis with scaling and root planning of the pathological periodontal pockets and these pockets were irrigated with the same composition. This composition as an aqueous solution was applied into the pathological pockets with a syringe for even greater effectiveness. After the treatment none of the patients suffered from periodontitis after six months.

For the same reasons that the above mentioned solution is active against most micro organisms in the mouth, Gingivitis can be treated by rinsing the mouth during two minutes twice a day during fourteen days. In heavy cases of illness cotton cloths soaked in the rinse can be applied directly around the teeth in contact with the gingiva.

Considering the similarity between oral and vaginal mucous tissues this therapy, i.e. applying a composition according to the present invention, will also be effective against micro organisms in the vagina (vaginose).

The invention claimed is:

1. A cleansing composition configured for use in the treatment of periodontitis, the cleansing composition comprising:
    an anti-microbial agent selected from the group consisting of a hydroxy acid, citric acid, acetyl salicylic acid, butyric acid, lactic acid, tartaric acid, acetic acid, malic acid or mixtures thereof,
    ammonium in an amount of between 0.1 and 0.8 wt %, and
    a combination of NaHCO$_3$ in an amount of between 0.1 to 2.5 wt % and salicylic acid,
    wherein the pH of the composition is between 1 and 5.

2. The cleansing composition according to claim 1, wherein the salicylic acid is present in the composition in an amount between 0.005 and 1 wt %.

3. The cleansing composition according to claim 1, wherein the amount of ammonium in the composition is between 0.1 and 0.5 wt %.

4. The cleansing composition according to claim 1, wherein the amount of anti-microbial agent in the composition is between 1.0 and 50 wt %.

5. The cleansing composition according to claim 1, wherein the anti-microbial agent is acetic acid and the amount of acetic acid in the composition is between 0.05 and 10 wt %.

6. The cleansing composition according to claim 1, wherein the anti-microbial agent is tartaric acid and the amount of tartaric acid in the composition is between 0.5 and 10 wt %.

7. The cleansing composition according to claim 1, wherein the amount of the ammonium is between 0.1 and 0.3 wt % of the composition, the amount of anti-microbial agent is between 30 to 45 wt % of the composition and the pH is between 2 and 4.

8. The cleansing composition according to claim 1, wherein the amount of anti-microbial agent is between 1 and 8 wt % of the composition and the pH is between 2 and 4.

9. The cleansing composition according to claim 7, wherein the anti-microbial agent is tartaric acid and/or acetic acid.

10. The cleansing composition according to claim 1, further comprising a fluoride source.

11. The cleansing composition according to claim 10, wherein the fluoride source is NH$_2$F, sodium fluoride, calcium fluoride, potassium fluoride, lithium fluoride, aluminium fluoride, zinc fluoride, zirconium fluoride, sodium monofluoro-phosphate, acidulated phosphate, fluoride, stannous chloro fluoride, magnesium fluoride, potassium trifluorostannous, titanium fluoride, iron fluoride, or stannous hexafluoro-zirconate.

12. The cleansing composition according to claim 11, wherein the composition comprises between 0.05 and 0.5 wt % NH$_2$F and/or NaF.

13. The cleansing composition according to claim 1, wherein the composition comprises enzymes.

14. The cleansing composition according to claim 1, wherein the composition comprises colourings, flavourings and/or stabilisers.

* * * * *